United States Patent
Climax et al.

(10) Patent No.: US 10,716,773 B2
(45) Date of Patent: *Jul. 21, 2020

(54) COMPOSITIONS COMPRISING 15-HEPE AND METHODS OF TREATING OR PREVENTING CANCER AND NEUROLOGIC DISEASE

(71) Applicant: Afimmune Limited, Dublin (IE)

(72) Inventors: John Climax, Dublin (IE); David Coughlan, Dublin (IE)

(73) Assignee: Afimmune Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,508

(22) Filed: Jan. 25, 2018

(65) Prior Publication Data

US 2018/0147173 A1    May 31, 2018

Related U.S. Application Data

(63) Continuation of application No. 15/216,345, filed on Jul. 21, 2016, now abandoned.

(60) Provisional application No. 62/195,138, filed on Jul. 21, 2015.

(51) Int. Cl.
*A61K 31/202* (2006.01)
*A61K 31/232* (2006.01)
*A61N 5/10* (2006.01)

(52) U.S. Cl.
CPC ........ *A61K 31/202* (2013.01); *A61K 31/232* (2013.01); *A61N 2005/1098* (2013.01)

(58) Field of Classification Search
CPC ............................ A61K 31/202; A61K 31/232
See application file for complete search history.

(56) References Cited

U.S. PATENT DOCUMENTS

| | | | |
|---|---|---|---|
| 8,293,790 B2 | 10/2012 | Manku et al. | |
| 9,050,308 B2 | 6/2015 | Maines et al. | |
| 9,056,086 B2* | 6/2015 | Manku | A61K 31/202 |
| 9,855,238 B2 | 1/2018 | Coughlan et al. | |
| 10,231,945 B2* | 3/2019 | Coughlan | A61K 31/202 |
| 2002/0055538 A1 | 5/2002 | Serhan et al. | |
| 2004/0043013 A1 | 3/2004 | McCleary | |
| 2005/0239889 A1 | 10/2005 | Gosselin | |
| 2006/0009522 A1 | 1/2006 | Dana et al. | |
| 2006/0078625 A1 | 4/2006 | Rockway | |
| 2007/0105954 A1 | 5/2007 | Puri | |
| 2007/0248586 A1 | 10/2007 | Arterburn et al. | |
| 2010/0233724 A1 | 9/2010 | Watkins et al. | |
| 2011/0059885 A1 | 3/2011 | Lea et al. | |
| 2011/0105510 A1 | 5/2011 | Ishikawa | |
| 2012/0142773 A1 | 6/2012 | Kelliher et al. | |
| 2012/0213824 A1 | 8/2012 | Kelliher et al. | |
| 2012/0232147 A1 | 9/2012 | Manku et al. | |
| 2012/0264705 A1 | 10/2012 | Manku et al. | |
| 2012/0264824 A1 | 10/2012 | Mizuguchi et al. | |
| 2013/0101533 A1 | 4/2013 | Manku et al. | |
| 2013/0102575 A1 | 4/2013 | Manku et al. | |
| 2013/0267598 A1 | 10/2013 | Manku et al. | |
| 2013/0274338 A1 | 10/2013 | Manku et al. | |
| 2014/0079631 A1 | 3/2014 | Serhan et al. | |
| 2015/0079164 A1 | 3/2015 | Fraser et al. | |
| 2015/0196521 A1 | 7/2015 | Manku et al. | |

FOREIGN PATENT DOCUMENTS

| | | |
|---|---|---|
| AU | 2011253846 | 1/2012 |
| EP | 1571195 | 9/2005 |
| EP | 2762143 | 8/2014 |
| JP | H07126160 | 5/1995 |
| JP | H09505562 | 6/1997 |
| JP | 2000191525 | 7/2000 |
| JP | A2003525880 | 9/2003 |
| JP | 2005179211 | 7/2005 |
| JP | 2013517304 | 5/2013 |
| RU | 94002337 | 8/1996 |
| RU | 2205004 | 5/2003 |
| WO | WO2001/060778 | 8/2001 |
| WO | WO 02/096408 | 12/2002 |
| WO | WO 2003/063793 | 8/2003 |
| WO | WO2009/098454 | 8/2009 |
| WO | WO 2010/125340 | 11/2010 |
| WO | WO 2013/057284 | 4/2013 |
| WO | WO2013057284 | 4/2013 |
| WO | WO2013057287 | 4/2013 |
| WO | WO2013082265 | 6/2013 |
| WO | WO2013112876 | 8/2013 |
| WO | WO2013124479 | 8/2013 |
| WO | WO2013170006 | 11/2013 |
| WO | WO2014118097 | 8/2014 |
| WO | WO2016/113635 | 7/2016 |

OTHER PUBLICATIONS

Kim et al. (2008) M867, a Novel Selective Inhibitor of Caspase-3 Enhances Cell Death and Extends Tumor Growth Delay in Irradiated Lung Cancer Models. PLoS ONE 3(5): e2275 (12 pages) (Year: 2008).*
Ballard et al., "Alzheimer's disease," Lancet. 377:1019-1031 (Mar. 19, 2011).
Boston et al., "Ethyl-EPA in Alzheimer's disease—a pilot study," Prostaglandins, Leukotrienes and Essential Fatty Acids. 71:341-346 (Apr. 22, 2004).
D'Amelio et al., "Caspase-3 in the central nervous system: beyond apoptosis," Trends in Neuroscience 35(11):700-09 (Nov. 1, 2012) (Abstract only).
Frank, "Treatement of Huntington's Disease," Neurotherapeutics. 11:153-160 (Dec. 24, 2013).
Heshiki et al., "Constitutive Activation of Caspase-3 in Non-Apoptotic Oral Squamous Cell Carcinoma Cells," Journal of Cancer Science & Therapy 7(2):75-80 (Feb. 28, 2015).
International Search Report and Written Opinion dated Jun. 26, 2016 for Internation Appplicational No. PCT/IB2016/000202.
Kalia et al., "Pakinson's disease," Lancet. 386:896-912 (Aug. 29, 2015).

(Continued)

*Primary Examiner* — James D. Anderson
(74) *Attorney, Agent, or Firm* — Perkins Coie LLP

(57) ABSTRACT

The present disclosure provides compositions comprising 15-HEPE and methods of using same for treating and/or preventing cancer and neurological diseases in a subject in need thereof.

8 Claims, 1 Drawing Sheet

(56) References Cited

OTHER PUBLICATIONS

Ruocco et al., "Diatom-derived oxylipins induce cell death in sea urchin embryos activating caspase-8 and caspase 3/7," Aquatic Toxicology (Apr. 22, 2016) (Abstract only).
Vang et al., "15-lipoxygenase metabolites of gamma-linolenic acid/eicosapentaenoic acid supress growth and arachidonic acid metabolism in human prostatic adenocarcinoma cells: possible implications of dietary fatty acids," Prostaglandins Leukot Essent Fatty Acids 72(5):363-72 (May 2005) (Abstract only).
Zou et al., "Inhibition of the HER2 pathway by n-3 polyunsaturated fatty acids prevents breast cancer in fat-1 transgenic mice," Journal of Lipid Research 54(12):3453-3463 (Dec. 1, 2013).
Boston et al., "Ethyl-EPA in Alzheimer's disease—a pilot study," Prostaglandins, Leukotrienes and Essential Fatty Acids. 71(5):341-346 (publication date: Nov. 2004).
Kajikawa et al., "Eicosapentaenoic acid attenuates progression of hepatic fibrosis with inhibition of reactive oxygen species production in rats fed methionine- and choline-deficient diet," Dig Dis Sci 56(4):1065-74 (publication date: Apr. 2011, epublication date: Sep. 17, 2010).
Das, "A defect in the activities of $\Delta^6$ and $\Delta^5$ desaturases and pro-resolution bioactive lipids in the pathobiology of non-alcoholic fatty liver disease," World Journal of Diabetes 2(11):176-188 (publication date: Nov. 15, 2011).
Ishii et al., "Eicosapentaenoic acid ameliorates steatohepatitis and hepatocellular carcinoma in hepatocyte-specific Pten-deficient mice", Journal of Hepatology, 2009, pp. 562-571 (publication date: Mar. 1, 2009, epublication date: Dec. 27, 2008).
Masterton et al., "Review article: omega-3 fatty acids—a promising novel therapy for non-alcoholic fatty liver disease," Alimentary Pharmacology & Therapeutics, 31(7):679-692 (publication date: Apr. 30, 2010, epublication date: Mar. 1, 2010).
Nguyen et al., "Mechanisms for anti-inflammatory effects of 1-[15(S)-hydroxyeicosapentaenoyl] lysophosphatidylcholine, administered intraperitoneally, in zymosan A-induced peritonitis," British Journal of Pharmacology 162(5):1119-1135 (publication date: Mar. 2011, epublication date: Nov. 22, 2010).
Tanaka, Naoki et al., "Highly Purified Eicosapentaenoic Acid Treatment Improves Nonalcoholic Steatohepatitis," Journal of Clinical Gastroenterology, vol. 42, No. 4, pp. 413-418 (publication date: Apr. 1, 2008).
Flachs et al., "Synergistic induction of lipid catabolism and anti-inflammatory lipids in white fat of dietary obese mice in response to calorie restriction and n-3 fatty acids", 2011, 54:2626-2638.
Kendall et al., "Distribution of Bioactive Lipid Mediators in Human Skin," The Journ. of Investigative Dermatology. (2015), 00, 1-11.
Miller et al., "Dietary Supplementation with Ethyl Ester Concentrates of Fish Oil (N-3) and Borage Oil (N-6) Polyunsaturated Fatty Acids Induces Epidermal Generation of Local Putative Anti-Inflammatory Metabolites," The Journ. of Invest. Dermatol., vol. 96, No. 1, pp. 98-103 (1991).
Miller et al., "Guinea Pig Epidermins Generates Putative Anti-Inflammatory Metabolites from Fish Oil Polyunsaturated Acids," Lipids, vol. 24, No. 12 (1989).
PCT Application No. PCT/IB2016/000202, International Search Report and Written Opinion, dated Jun. 6, 2016, 4 pages.
Vang K, et al., "15-lipoxygenase metabolites of gamma-linolenic acid/eicosapentaenoic acid suppress growth and arachidonic acid metabolism in human prostatic adenocarcinoma cells: Possible implications of dietary fatty acids", Prostaglandins Leukotrienes and essential fatty acids, Churchill Lingstone, Edinburgh, vol. 72, No. 5, pp. 363-372 (2005).
Barnes, "Mediators of Chronic Obstructive Pulmonary Disease," Pharmacol Rev 56(4):515-48 (Dec. 2004).
Brooks et al., "The fatty acid oxidation product 15-A3t-isoprostane is a potent inhibitor of NFκB transcription and macrophage transformation," Journal of Neurochemistry 119:604-616 (Nov. 2011).
Kajikawa et al., "Eicosapentaenoic acid attenuates progression of hepatic fibrosis with inhibition of reactive oxygen species production in rats fed methionine- and choline-deficient diet," Dig Dis Sci 56(4):1065-74 (Aug. 12, 2010).
Parker et al., "Omega-3 supplementation and non-alcoholic fatty liver disease: a systematic review and meta-analysis," J. Hepatol. 56(4):944-51 (Apr. 2012).
Miller et al., "Guinea Pig Epidermis Generates Putative Anti-Inflammatory Metabolites from Fish Oil Polyunsaturated Acids," Lipids 24(12):998-1003 (publication date: Dec. 1989).
Lam et al., "Transformation of 15-Hydroperoxyeicosapentaenoic acid into mono-and dihydroeicosapentaenoic acids by human platelets," Drugs Affecting Leukotrienes and Other Eicosanoid Pathways 95:167-180 (1985).
Román, Studies of anti-cancer and anti-inflammatory activity of bioactive compounds isolated from terrestrial and marine aqueous media, abstract accessed at: https://idus.us.es/xmlui/handle/11441/51306, (publication date: Mar. 21, 2014) (Abstract only).

* cited by examiner

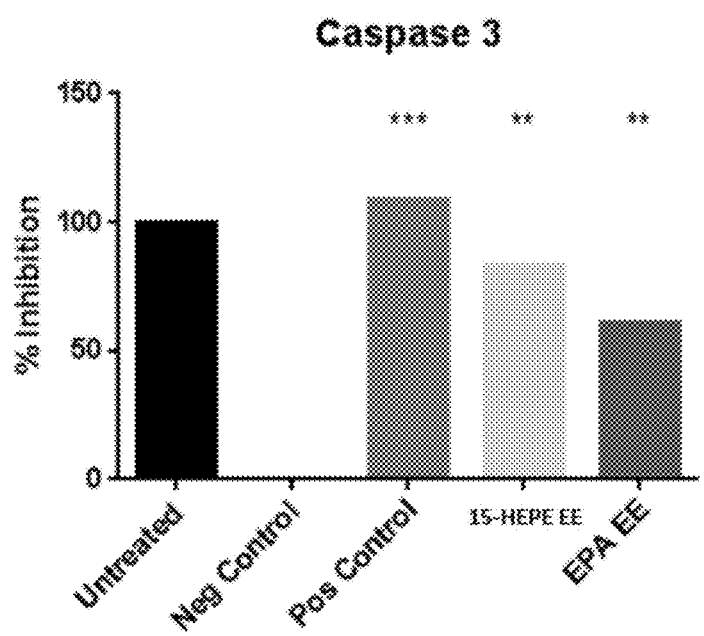

COMPOSITIONS COMPRISING 15-HEPE AND METHODS OF TREATING OR PREVENTING CANCER AND NEUROLOGIC DISEASE

PRIORITY CLAIM

This application is a continuation of U.S. patent application Ser. No. 15/216,345, filed on Jul. 21, 2016, which claims priority to U.S. Provisional Patent Application Ser. No. 62/195,138, filed Jul. 21, 2015, the entire contents of which is incorporated herein by reference in its entirety.

FIELD

The present disclosure provides compositions, formulations and methods of treating or preventing cancer and neurologic diseases by administering a pharmaceutical composition comprising 15-hydroxyeicosapentaenoic acid (also referred to as 15-HEPE) or a derivative thereof to a subject in need thereof.

BACKGROUND

Apoptosis is a genetically regulated and tightly controlled process involved in eliminating defective cells from tissues. Under normal conditions, the rate of apoptosis and cellular proliferation are in balance, thereby maintaining homeostasis. Under certain disease states, apoptosis can be upregulated, creating an imbalance that creates to tissue damage and loss of function. Caspases are a group of cysteine proteases critical for apoptosis of eukaryotic cells. Activation of the caspase cascade, if completed, leads to activation of the terminal effector caspase-3—the terminal effector caspase.

SUMMARY

In some embodiments, the present disclosure provides methods of treating and/or preventing cancer in a subject in need thereof, the method comprising administering to the subject 15-HEPE or a derivative thereof or a composition comprising 15-HEPE or a derivative thereof. In some embodiments, the cancer is selected from carcinoma, CNS cancer, liver cancer, hepatocellular carcinoma, skin cancer, prostate cancer, breast cancer and lung cancer.

In some embodiments, the present disclosure provides methods of treating and/or preventing a neurological disorder in a subject in need thereof, the method comprising administering to the subject 15-HEPE or a derivative thereof or a composition comprising 15-HEPE or a derivative thereof. In some embodiments, the neurological disorder is selected from catalepsy, epilepsy, encephalitis, meningitis, migraine, Huntington's, Alzheimer's, Parkinson's, and multiple sclerosis.

In some embodiments, the present disclosure provides uses of 15-HEPE in the manufacture of a medicament for treating and/or preventing cancer or a neurological disorder in a subject.

In some embodiments, the present disclosure provides a method of promoting normal cell proliferation in a subject in need thereof, the method comprising administering to the subject 15-HEPE or a composition comprising 15-HEPE.

In some embodiments, the present disclosure provides q method of preventing cell death in an organ in a subject in need thereof, the method comprising administering to the subject 15-HEPE or a composition comprising 15-HEPE.

In some embodiments, the present disclosure provides a method of reducing cancerous tumor proliferation in a subject in need thereof, the method comprising administering to the subject 15-HEPE or a composition comprising 15-HEPE.

In some embodiments, the present disclosure provides a method of delaying tumor growth in a subject in need thereof, the method comprising administering to the subject 15-HEPE or a composition comprising 15-HEPE.

In some embodiments, the present disclosure provides method of inhibiting caspase-3 activity in a subject in need thereof, the method comprising administering to the subject 15-HEPE or a composition comprising 15-HEPE.

In some embodiments, the present disclosure provides a method of sensitizing cancer cells to radiation therapy in a subject in need thereof, the method comprising administering to the subject 15-HEPE or a composition comprising 15-HEPE and concurrently or thereafter treating cancer cells in the subject with radiation.

Other features and advantages of the technology disclosed herein will be apparent from the following detailed description.

BRIEF DESCRIPTION OF THE DRAWINGS

FIG. 1 shows that at the concentration of 100 µg/ml, compounds 15(S)-HEPE EE and EPA EE both displayed a clear inhibitory effect on caspase-3/7 activity (with a stronger effect for compound 15(S)-HEPE EE).

DETAILED DESCRIPTION

The present disclosure provides compositions comprising 15-HEPE, and methods of using same for treating and/or preventing cancer or a neurological disease in a subject in need thereof.

15-Hydroxy-eicosa-5,8,11,13,17-pentaenoic acid is a functionalized fatty acid having the general structure shown in Formula (I).

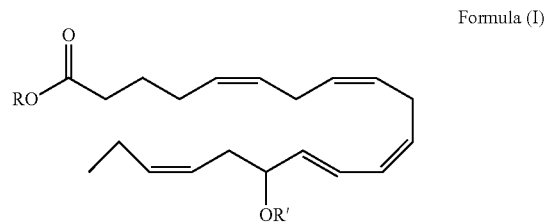

Formula (I)

15-HEPE can be synthesized from eicosapentaenoic acid (EPA) according to methods known in the art. As used herein, the term "15-HEPE" may refer to 15-HEPE in its free acid form (e.g, 15-hydroxy-eicosa-5,8,11,13,17-pentaenoic acid; R=R'=H in Formula (I)) and/or a derivative thereof, such as a pharmaceutically acceptable ester (R≠H), a conjugate, or a salt (R is an ion) consistent with Formula (I), or mixtures of any of the foregoing. A derivative of 15-HEPE (e.g., R≠H and/or R'≠H) may be used instead. In some embodiments, the 15-HEPE is used in the free acid form (i.e., R=H). Alternatively, pharmaceutically acceptable esters or salts of 15-HEPE are used in certain embodiments of the present disclosure. In some embodiments, the 15-HEPE is in the form of a $C_{1-4}$ alkyl ester such as methyl ester (R=CH$_3$) or ethyl ester (R=CH$_2$CH$_3$) form. 15-HEPE is a chiral molecule and may be used in the 15(S)— or 15(R)— enantiomeric form, in an enantiomerically enriched form, or as a racemic mixture. Used herein, "15-HEPE" includes all such forms, with no limitation as to stereospecificity. In another embodiment, the 15-HEPE comprises the 15(S) form: 15(S)-hydroxy-(5Z,8Z,11Z,13E, 17Z)-eicosapentaenoic acid, or a derivative thereof. In some embodiments, the 15-HEPE may be used in the form of the ethyl ester.

As used herein, "EPA" refers to eicosa-5,8,11,14,17-pentaenoic acid, also known as 20:5n-3, an omega-3 fatty acid. EPA is readily obtainable through commercial sources.

Accordingly, in one aspect of the present disclosure, a method of treating and/or preventing cancer or a neurological disease in a subject is provided, comprising administering to the subject a therapeutically effective amount of a composition comprising 15-HEPE.

The present disclosure provides 15-HEPE, or a composition comprising 15-HEPE, for use in the treatment and/or prevention of cancer or a neurological disease.

The present disclosure provides a use of 15-HEPE, or a composition comprising 15-HEPE, in the manufacture of a medicament for treating and/or preventing cancer or a neurological disease.

The present disclosure also provides formulations of 15-HEPE and formulations comprising 15-HEPE and methods of using these formulations for treating and/or preventing cancer or a neurological disorder.

The present disclosure further provides a pharmaceutical composition for oral delivery, comprising 15-HEPE. That composition may comprise a pharmaceutically acceptable excipient. The 15-HEPE may be in any form as discussed herein. The 15-HEPE may be present from about 50 mg to about 3000 mg.

15-Hydroxyeicosapentaenoic acid (15-HEPE)

In one embodiment, compositions of the present disclosure comprise 15-HEPE as an active ingredient. 15-HEPE is the abbreviation for 15-hydroxyeicosapentaenoic acid, a compound that can be synthesized via methods known in the art, such as exposure of eicospentaenoic acid to the enzyme 15-lipoxygenase. As used herein, the term "15-HEPE" refers to 15-HEPE in its free acid form (e.g., 15-hydroxyeicosapentaenoic acid) and/or a pharmaceutically acceptable ester, conjugate or salt thereof, or mixtures of any of the foregoing. A derivative of 15-HEPE may be used instead, though this does not include any derivative compound missing the hydroxy group of 15-HEPE. The term "pharmaceutically acceptable" in the present context means that the substance in question does not produce unacceptable toxicity to the subject or interaction with other components of the composition.

In one embodiment, the 15-HEPE is in the form of an ester (also referred to herein as E-15-HEPE, 15-HEPE EE, or ethyl-15-HEPE). In another embodiment, the 15-HEPE comprises a $C_1$-$C_5$ alkyl ester of 15-HEPE. In another embodiment, the 15-HEPE comprises 15-HEPE methyl ester, 15-HEPE propyl ester, or 15-HEPE butyl ester. In still another embodiment, the 15-HEPE comprises the optically active 15(S)-Hydroxy-(5Z,8Z,11Z,13E,17Z)-eicosapentaenoic acid. This isomer may be used in any of the forms discussed above.

In another embodiment, the 15-HEPE comprises lithium 15-HEPE, mono-, di- or triglyceride 15-HEPE or any other ester or salt of 15-HEPE, or the free acid form of 15-HEPE.

In various embodiments, the present disclosure provides pharmaceutical compositions, for example orally deliverable compositions, comprising 15-HEPE. In one embodiment, the compositions comprise a therapeutically effective amount of 15-HEPE. In one embodiment, the pharmaceutical composition comprises about 0.1% to about 99%, about 1% to about 95%, about 5% to about 90% by weight of 15-HEPE.

In one embodiment, the pharmaceutical composition comprises about at least about 70%, at least about 80% or at least about 90%, by weight, of 15-HEPE. In one embodiment, the pharmaceutical composition comprises at least about 50%, at least about 60%, at least about 70%, at least about 80% or at least about 90%, by weight of 15-HEPE.

In another embodiment, 15-HEPE is present in a composition of the present disclosure in an amount of about 1 mg to about 10,000 mg, 25 mg to about 7500 mg, about 25 mg to about 5000 mg, about 50 mg to about 5000 mg, about 50 mg to about 3000 mg, about 75 mg to about 2500 mg, or about 100 mg to about 1000 mg, for example about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, 15-HEPE present in a composition of the present disclosure comprises at least 90% by weight 15-HEPE. 15-HEPE compositions can comprise even higher purity 15-HEPE, for example at least 95% by weight 15-HEPE or at least 97% by weight 15-HEPE, wherein the 15-HEPE is any form of 15-HEPE as set forth herein. The purity of 15-HEPE can further be defined (e.g. impurity profile) by any of the descriptions of 15-HEPE provided herein.

Above are discussed the amounts of the 15-HEPE in the pharmaceutical composition and their purity. The nature of the essential fatty acids and their synthesis is such that the 15-HEPE composition may include moieties from other essential fatty acids in the essential fatty acid metabolic cascade.

In one embodiment, a composition of the present disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of other omega-3 fatty acids including alpha linolenic acid, stearidonic acid, docosahexaenoic acid (DHA) or derivatives thereof. In other embodiments there is substantially no, or no such other omega-3 fatty acids present.

In another embodiment, 15-HEPE represents at least about 60%, at least about 70%, at least about 80%, at least about 90%, at least about 95%, at least about 97%, at least about 98%, at least about 99%, or 100%, by weight, of all fatty acids present in a composition of the present disclosure.

There may be present some residual eicosapentaenoic acid from the synthesis of the 15-HEPE. There may be not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight EPA. Alternatively, there is substantially no, or no, EPA in a form which has not been modified to the hydroxyl-form.

Dosage Forms

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In some embodiments, compositions of the present disclosure are in the form of orally deliverable dosage forms or units. Non-limiting examples of suitable dosage forms include tablets (e.g. suspension tablets, bite suspension tablets, rapid dispersion tablets, chewable tablets, etc), caplets, capsules (e.g. a soft or a hard gelatin capsule or HPMC capsule), lozenges, sachets, cachets, troches, pellets, suspension, elixirs, syrups or any other solid dosage form reasonably adapted for oral administration. The terms "oral delivery" and "oral administration" herein include any form of delivery wherein the agent or composition is placed in the mouth of the subject under treatment, whether swallowed or not. This therefore includes buccal and sublingual administration, as well as esophageal administration.

Alternatively, compositions of the present disclosure can also be formulated for rectal, topical, or parenteral (e.g. subcutaneous, intramuscular, intravenous and intradermal or infusion) delivery.

In discussing the amount of 15-HEPE in a composition of the present disclosure, this may be split over several dosage forms. There is a limit as to the size for oral administration. If a subject is to be administered up to 4 g 15-HEPE a day, this may be by up to 4 capsules, each providing 1 g 15-HEPE, or up to 16 capsules, each providing 0.25 g 15-HEPE, for example, 1, 2, 3, 4, 5, 6, 7, 8, 9, 10, 11, 12, 13, 14, 15, or 16 capsules per day, each providing about 0.25 g to about 1 g of 15-HEPE.

Compositions of the present disclosure can be in the form of liquid dosage forms or dose units to be imbibed directly or they can be mixed with food or beverage prior to ingestion. Non-limiting examples of suitable liquid dosage forms include solutions, suspensions, elixirs, syrups, liquid aerosol formulations, and the like.

In another embodiment, compositions of the present disclosure comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition. By way of example only, a pharmaceutical composition according to the present disclosure may comprise one or more of: antioxidants, surfactants, preservatives, flavouring agents, co-solvents, viscosity aids, suspension aids, and lipophilic phases.

In one embodiment, the pharmaceutical composition comprises one or more antioxidants such as ascorbic acid, palmitic acid, ascorbyl palmitate, α-tocopherol, idebenone, ubiquinone, ferulic acid, coenzyme Q10, lycopene, green tea, catechins, epigallocatechin 3-gallate (EGCG), green tea polyphenols (GTP), silymarin, coffeeberry, resveratrol, grape seed, pomegranate extracts, genisten, pycnogenol, niacinamide, butylated hydroxyltoluene (BHT), butylated hydroxylanisol (BHA), and the like. In one embodiment, the pharmaceutical composition comprises about 0.01 wt. % to about 2 wt. % of an antioxidant, for example about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.11 wt. %, about 0.12 wt. %, about 0.13 wt. %, about 0.14 wt. %, about 0.15 wt. %, about 0.16 wt. %, about 0.17 wt. %, about 0.18 wt. %, about 0.19 wt. %, about 0.2 wt. %, about 0.21 wt. %, about 0.22 wt. %, about 0.23 wt. %, about 0.24 wt. %, about 0.25 wt. %, about 0.26 wt. %, about 0.27 wt. %, about 0.28 wt. %, about 0.29 wt. %, about 0.3 wt. %, about 0.31 wt. %, about 0.32 wt. %, about 0.33 wt. %, about 0.34 wt. %, about 0.35 wt. %, about 0.36 wt. %, about 0.37 wt. %, about 0.38 wt. %, about 0.39 wt. %, about 0.4 wt. %, about 0.41 wt. %, about 0.42 wt. %, about 0.43 wt. %, about 0.44 wt. %, about 0.45 wt. %, about 0.46 wt. %, about 0.47 wt. %, about 0.48 wt. %, about 0.49 wt. %, about 0.5 wt. %, about 0.51 wt. %, about 0.52 wt. %, about 0.53 wt. %, about 0.54 wt. %, about 0.55 wt. %, about 0.56 wt. %, about 0.57 wt. %, about 0.58 wt. %, about 0.59 wt. %, about 0.6 wt. %, about 0.61 wt. %, about 0.62 wt. %, about 0.63 wt. %, about 0.64 wt. %, about 0.65 wt. %, about 0.66 wt. %, about 0.67 wt. %, about 0.68 wt. %, about 0.69 wt. %, about 0.7 wt. %, about 0.71 wt. %, about 0.72 wt. %, about 0.73 wt. %, about 0.74 wt. %, about 0.75 wt. %, about 0.76 wt. %, about 0.77 wt. %, about 0.78 wt. %, about 0.79 wt. %, about 0.8 wt. %, about 0.81 wt. %, about 0.82 wt. %, about 0.83 wt. %, about 0.84 wt. %, about 0.85 wt. %, about 0.86 wt. %, about 0.87 wt. %, about 0.88 wt. %, about 0.89 wt. %, about 0.9 wt. %, about 0.91 wt. %, about 0.92 wt. %, about 0.93 wt. %, about 0.94 wt. %, about 0.95 wt. %, about 0.96 wt. %, about 0.97 wt. %, about 0.98 wt. %, about 0.99 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, or about 2 wt. % of the one or more antioxidant.

Therapeutic Methods

The compositions and formulations disclosed herein may be used in the treatment of cancer. In one embodiment the cancer is associated with an organ or tissue associated with the CNS, a lung, a liver, a heart, a kidney, a bowel, a stomach, one or more eyes, mediastinum, bone marrow, retroperitoneaum, skin, an intestine, a joint, a reproductive organ, a prostate, a breast or a combination thereof. In some embodiments, the 15-HEPE is administered to reduce tumor proliferation or delay tumor growth.

In some embodiments, the 15-HEPE is administered to promote normal cell proliferation.

In some embodiments, the 15-HEPE is administered to radiosensitize cancer cells, and can be used a radiosensitizer in radiation therapy.

In some embodiments, the composition is orally administered.

In some embodiments, the 15-HEPE is the only active ingredient in the composition. In other embodiments, the composition further comprises an additional agent for affecting the fibrosis therapy.

In some embodiments of the methods disclosed herein, the 15-HEPE is the only active ingredient in the composition. In some embodiments, the composition further comprises an additional agent for affecting the cancer or CNS disease.

In some embodiments, the method further comprises identifying the subject as having cancer or CNS disease before administering the composition comprising 15-HEPE. In some embodiments, the method further comprises identifying the subject as having an increased risk of developing cancer or CNS disease before administering the composition comprising 15-HEPE. In some embodiments, the step of identifying comprises screening for a genetic mutation in a nucleic acid molecule associated with the subject. In some embodiments, the step of identifying comprises obtaining an analysis of blood and/or serum associated with the subject. In some embodiments, the step of identifying comprises examining a tissue associated with the subject. In some embodiments, the step of examining comprises analyzing a histological tissue sample (e.g., a biopsy) associated with the subject.

In some embodiments, the present disclosure provides uses of 15-HEPE in the manufacture of a medicament for treating and/or preventing cancer or a neurological disorder in a subject.

In some embodiments, the present disclosure provides a method of promoting normal cell proliferation in a subject in need thereof, the method comprising administering to the subject 15-HEPE or a composition comprising 15-HEPE.

In some embodiments, the present disclosure provides a method of preventing cell death in an organ in a subject in need thereof, the method comprising administering to the subject 15-HEPE or a composition comprising 15-HEPE.

In some embodiments, the present disclosure provides a method of reducing cancerous tumor proliferation in a subject in need thereof, the method comprising administering to the subject 15-HEPE or a composition comprising 15-HEPE.

In some embodiments, the present disclosure provides a method of delaying tumor growth in a subject in need thereof, the method comprising administering to the subject 15-HEPE or a composition comprising 15-HEPE.

In some embodiments, the present disclosure provides a method of inhibiting caspase-3 activity in a subject in need thereof, the method comprising administering to the subject 15-HEPE or a composition comprising 15-HEPE.

In some embodiments, the present disclosure provides a method of sensitizing cancer cells to radiation therapy in a subject in need thereof, the method comprising administering to the subject 15-HEPE or a composition comprising 15-HEPE and concurrently or thereafter treating cancer cells in the subject with radiation.

In one embodiment, the method comprises administering a pharmaceutical composition as disclosed herein to a subject once per day, twice per day, three times per day, or more than three times per day.

Unless otherwise defined, all technical and scientific terms used herein have the same meaning as commonly understood by one of ordinary skill in the art to which this present disclosure pertains. Although methods and materials similar or equivalent to those described herein can be used in the practice of the present disclosure, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

While the present disclosure is capable of being embodied in various forms, the present description below of several embodiments is made with the understanding that the present disclosure is to be considered as an exemplification of the present disclosure, and is not intended to limit the technology disclosed herein to the specific embodiments illustrated. Headings are provided for convenience only and are not to be construed to limit the technology disclosed herein in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

As used herein, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

An "effective amount," as used herein, refers to the amount of an active composition that is required to confer a therapeutic effect on the subject. A "therapeutically effective amount," as used herein, refers to a sufficient amount of an agent or a compound being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, in some embodiments, an "effective amount" for therapeutic uses is the amount of the composition including a compound as disclosed herein required to provide a clinically significant decrease in disease symptoms without undue adverse side effects. In some embodiments, an appropriate "effective amount" in any individual case is determined using techniques, such as a dose escalation study. The term "therapeutically effective amount" includes, for example, a prophylactically effective amount. In other embodiments, an "effective amount" of a compound disclosed herein, such as a compound of Formula (I), is an amount effective to achieve a desired pharmacologic effect or therapeutic improvement without undue adverse side effects. In other embodiments, it is understood that "an effect amount" or "a therapeutically effective amount" varies from subject to subject, due to variation in metabolism, age, weight, general condition of the subject, the condition being treated, the severity of the condition being treated, and the judgment of the prescribing physician. The term "pharmaceutically acceptable" in the present context means that the substance in question does not produce unacceptable toxicity to the subject or interaction with other components of the composition.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLE

The potential inhibitory effect of compounds 15(S)-HEPE EE and EPA EE was evaluated on staurosporine-induced caspase activation in normal human dermal fibroblasts (NHDF). More specifically, at the end of the treatments with the test compounds in staurosporine-activated NHDF, the caspase 3/7 activity was measured after cell lysis using a specific fluorogenic substrate.

Normal human dermal fibroblasts (NHDF) were used at the $8^{th}$ passage. Cells were cultured at 37° C., 5% $CO_2$ in DMEM supplemented with L-glutamine 2 mM, 50 U/ml Penicillin, 50 µg/ml Streptomycin and 10% Foetal calf serum (FCS).

Test compounds are shown in Table 1.

TABLE 1

| Test Compounds | | | |
|---|---|---|---|
| Test compound | Aspect/Storage | Stock solution | Test concentrations |
| 15(S)-HEPE EE<br>Batch no 2540B-1502<br>MW: 346.5<br>Purity: 96.7%<br>MV150413-1 | Liquid<br>Storage: +4° C.<br>protected from light | 100 mg/ml in DMSO | 0.001, 0.01, 0.1, 1, 10<br>and 100 µg/ml |

TABLE 1-continued

Test Compounds

| Test compound | Aspect/Storage | Stock solution | Test concentrations |
|---|---|---|---|
| EPA EE<br>Batch no U-99E-JY8-Y<br>MW: 330.5<br>MV150413-4 | Liquid<br>Storage: +4° C.<br>protected from light | 100 mg/ml in ethanol | 0.001, 0.01, 0.1, 1, 10 and 100 µg/ml |

Fibroblasts were seeded in 24-well plates and cultured for 24 hours in culture medium. The medium was then removed and replaced by assay medium containing or not (control) the test compounds and cells were pre-incubated for 24 hours. After pre-incubation, the medium was replaced with assay medium containing the inducer (staurosporine at 100 nM) and containing or not (control) the test compounds. The cells were then incubated for 24 hours. Non-stimulated controls (without inducer) were performed in parallel. All experimental conditions were performed in n=3.

At the end of incubation, the cell layers were lysed for caspase 3/7 activity measurement and protein quantification was also performed on other dedicated culture plates performed in parallel with identical treatments. Enzyme activity assay and protein quantification assay were performed in separated plates due to the fact that DTT used in the lysis buffer for caspase activity interferes with protein quantification.

For caspase 3/7 activity measurement, cell layers were first detached using trypsin treatment and transferred in microtubes before performing the cell lysis.

The positive control was recombinant human active caspase-3 (BD Biosciences, ref. 556471), tested at 50 ng/ml.

Cell lysates of fibroblasts, were either treated or not (controls) with the test compounds for 48 hours, and with staurosporine during the last 24 hours of incubation (except for the non-stimulated control) with the following buffers and reagents:

Lysis buffer: HEPES buffer (pH 7.4) containing EDTA, Triton X-100, NP-40 and DTT Assay Buffer: HEPES buffer (pH 7.4) containing NaCl, EDTA, NP-40, glycerol and DTT Substrate: Ac-DEVD-AMC, tested at 10 µM (stock solution at 1.5 mM in DMSO)

Reference inhibitor: Ac-DEVD-CHO, caspase 3 inhibitor, tested at 0.1 µM

Cell lysis was achieved by adding 100 µl of lysis buffer/microtube on the cell pellets and a freeze/thaw cycle.

Ac-DEVD-AMC is a synthetic tetrapeptide fluorogenic substrate for caspase-3 and caspase-7 and contains the amino acid sequence of the PARP cleavage site at Asp-216. Thus the tetrapeptide substrate can be used to identify and quantify the caspase-3/7 activity. Enzymes cleave the tetrapeptide between D and AMC resulting in the release of fluorogenic AMC, which can be quantified with a spectrofluorometer.

Cell lysates (30 µl/well) or recombinant human active caspase-3 were incubated in assay buffer, in presence of the substrate, for 3 hours at 37° C. under agitation (final volume 100 µl). The specificity of the reaction was evaluated by testing a stimulated control condition in presence of the caspase 3 specific inhibitor Ac-DEVD-CHO (0.1 µM). In parallel, an additional control (assay buffer containing the substrate) was also performed to determine the background signal.

At the end of incubation, the fluorescence intensity emitted by the reaction product (cleaved Ac-DEVD-AMC) was measured at wavelengths $\lambda_{ex}$ 380 nm and $\lambda_{em}$ 440 nm using a spectrofluorometer (SPECTRAmax® Gemini, Molecular Devices).

The results of the MTT reduction assay and the observation of the cell layers are shown in Tables 2 and 3, below.

In presence of the positive control (recombinant human active caspase 3, tested at 50 ng/ml), the detected caspase-3/7 activity was very strong (acellular control).

TABLE 2

Effect of 15(S)-HEPE EE on the viability of fibroblasts after 48 hours of incubation

| | Control | | 15(S)-HE PE EE<br>Stock solution prepared at<br>100 mg/ml in DM SO | | | | | | Unit µg/ml | |
| --- | --- | --- | --- | --- | --- | --- | --- | --- | --- | --- |
| | | | 0.001 | 0.01 | 0.1 | 1 | 10 | 30 | 100 | 300 |
| Visability (%) | 99 | 100 | 98 | 98 | 98 | 97 | 101 | 96 | 104 | 97 |
| | 103 | 99 | 99 | 90 | 99 | 96 | 100 | 103 | 103 | 98 |
| | 98 | 100 | 97 | 100 | 96 | 96 | 102 | 98 | 105 | 105 |
| Mean | 100 | | 98 | 96 | 97 | 97 | 101 | 99 | 104 | 100 |
| sem | 1 | | 1 | 3 | 1 | 0 | 1 | 2 | 0 | 3 |
| Morpholigical observations | + | | + | + | + | + | + | + | + | +.* |

Legend
+: normal population;
+/−: growth reduction;
−: toxicity;
0: cell mortality
g: grains of compound;
op: opacity of the compound;
*morphological modification;
ag: agglutinated cells
sem: Standard error of the mean (standard deviation divided by sample size square root)

TABLE 3

Effect of EPA EE on the viability of fibroblasts after 48 hours of incubation

| | Control | | EPA EE Stock solution prepared at 100 mg/ml in Ethanol | | | | | | Unit µg/ml | |
|---|---|---|---|---|---|---|---|---|---|---|
| | | | 0.001 | 0.01 | 0.1 | 1 | 10 | 30 | 100 | 300 |
| Visability (%) | 100 | 99 | 97 | 94 | 99 | 100 | 98 | 95 | 98 | 107 |
| | 101 | 100 | 104 | 98 | 98 | 95 | 100 | 93 | 100 | 106 |
| | 100 | 100 | 99 | 101 | 99 | 95 | 94 | 99 | 102 | 105 |
| Mean | 100 | | 100 | 98 | 99 | 97 | 97 | 96 | 100 | 106 |
| sem | 0 | | 2 | 2 | 0 | 1 | 2 | 2 | 1 | 1 |
| Morpholigical observations | + | | + | + | + | + | + | + | + | + |

Legend
+: normal population;
+/−: growth reduction;
−: toxicity;
0: cell mortality
g: grains of compound;
op: opacity of the compound;
*morphological modification;
ag: agglutinated cells
sem: Standard error of the mean (standard deviation divided by sample size square root)

In control condition (Tables 4-5), the basal caspase-3/7 activity in non-stimulated fibroblasts was limited with a signal rather close to the background control. The apoptosis inducer staurosporine, tested at 100 nM, showed a strong stimulating effect on caspase-3/7 activity with a 10 fold increase between staurosporine-stimulated conditions and non-stimulated conditions (when considering the caspase-3/7 activity normalized versus protein quantity). Moreover, this activity was fully inhibited when adding in the reaction mix, the inhibitor Ac-DEVD-CHO at 0.1 µM, thus confirming the specificity of the detected caspase-3/7 activity. These results validated the assay.

In this assay, the 2 test compounds, i.e., 15(S)-HEPE EE and EPA EE were tested at the same range of 6 concentrations: 0.001, 0.01, 0.1, 1, 10 and 100 µg/ml.

Compound 15(S)-HEPE EE showed no effect on caspase-3/7 activity when tested from 0.001 to 10 µg/ml. However, at the highest concentration (100 µg/ml), this compound displayed opposite effects, with a very strong inhibitory effect for 15(S)-HEPE EE (83% of inhibition).

Compound EPA EE, showed no effect on caspase-3/7 activity when tested from 0.001 to 10 µg/ml. Compound EPA EE, at highest test concentration, displayed a strong inhibitory effect on caspase-3/7 activity (61% of inhibition).

At the concentration of 100 µg/ml, compounds 15(S)-HEPE EE and EPA EE both displayed a clear inhibitory effect on caspase-3/7 activity (with a stronger effect for compound 15(S)-HEPE EE).

TABLE 4

Effect of 15(S)-HEPE EE on staurosporine-induced caspase-3/7 activity in NHD.

| Treatment | | | Basic data | | | | | | | | Normalized data | | | |
|---|---|---|---|---|---|---|---|---|---|---|---|---|---|---|
| | | Caspase-3/7 activity (Fluorescence) | Caspase-3/7 activity - Background (Fluorescence) | Proteins | | Caspese-3/7 activity/proteins | Mean | sem | % stimulated control | sem | | | sem | |
| Test compound | Concentration | 380 nm/440 nm- AU | 380 nm/440 nm- AU | (mg/ml) | (mg) | (AU/mg) | (AU/mg) | (AU/mg) | | (%) | $P^{(1)}$ | % inhibition | (%) | $P^{(1)}$ |
| Background Assay butter + caspase-3/7 substrate | * | 332 334 323 | * | * | * | * | * | * | * | * | * | * | * | * |
| Positive control Recombirant human active Caspese-3 | 50 ng/ml | 10874 11045 11153 | 10544 10715 10823 | * | * | * | * | * | * | * | * | * | * | * |
| Non-stimulated Control condition | * | 493 478 530 | 163 149 200 | 0.716 0.724 0.661 | 0.021 0.022 0.020 | 7596 6838 10099 | 8178 | 255 | 10 | 1 | *** | 100 | 1 | *** |
| Control | * | 1559 1599 1445 | 1229 1369 1115 | 0.454 0.472 0.524 | 0.014 0.014 0.016 | 90232 96694 70952 | 85999 | 7722 | 100 | 2 | * | 0 | 10 | * |
| Ac-DEVO-CHO | 0.1 μm | 347 343 339 | 17 13 10 | 0.454 0.480 0.471 | 0.014 0.014 0.014 | 1254 934 674 | 954 | 155 | 1 | 0 | *** | 109 | 0 | *** |
| 16(8)-HE PE EE | 0.001 μg/ml | 1809 1753 1686 | 1479 1423 1396 | 0.452 0.366 0.428 | 0.014 0.011 0.013 | 109076 129611 105615 | 114767 | 7452 | 134 | 0 | ns | -37 | 10 | ns |
| | 0.01 μg/ml | 1495 1587 1789 | 1166 1258 1459 | 0.479 0.467 0.486 | 0.014 0.014 0.015 | 81085 89757 100075 | 90306 | 2455 | 106 | 0 | ns | -6 | 7 | ns |

TABLE 4-continued

Effect of 15(S)-HEPE EE on staurosporine-induced caspase-3/7 activity in NHD.

| Treatment | | Basic data | | | | | | | | Normalized data | | |
|---|---|---|---|---|---|---|---|---|---|---|---|---|
| | | Caspase-3/7 activity (Fluorescence) | Caspase-3/7 activity - Background (Fluorescence) | Proteins | | Caspese-3/7 activity/proteins | Mean | sem | % stimulated control | sem | | |
| Test compound | Concentration | 380 nm/440 nm- AU | 380 nm/440 nm- AU | (mg/ml) | (mg) | (AU/mg) | (AU/mg) | (AU/mg) | (%) | (%) | p$^{(1)}$ | % inhibition | sem (%) | p$^{(1)}$ |
| | 0.1 µg/ml | 1468 | 1139 | 0.468 | 0.014 | 81102 | 82485 | 15356 | 98 | 15 | ns | 4 | 20 | ns |
| | | 1697 | 1367 | 0.415 | 0.012 | 109799 | | | | | | | | |
| | | 1154 | 825 | 0.486 | 0.015 | 56654 | | | | | | | | |
| | 1 µg/ml | 1536 | 1206 | 0.465 | 0.014 | 86474 | 93200 | 2571 | 108 | 4 | ns | −9 | 2 | ns |
| | | 1600 | 1270 | 0.448 | 0.013 | 94481 | | | | | | | | |
| | | 1735 | 1406 | 0.475 | 0.014 | 93645 | | | | | | | | |
| | 10 µg/ml | 1439 | 1109 | 0.485 | 0.015 | 76241 | 80078 | 1250 | 93 | 2 | ns | 8 | 2 | ns |
| | | 1551 | 1221 | 0.500 | 0.015 | 81395 | | | | | | | | |
| | | 1514 | 1184 | 0.478 | 0.014 | 82597 | | | | | | | | |
| | 100 µg/ml | 663 | 324 | 0.545 | 0.016 | 15788 | 21632 | 1217 | 26 | 2 | ** | 83 | 2 | ** |
| | | 729 | 400 | 0.523 | 0.016 | 15464 | | | | | | | | |
| | | 660 | 320 | 0.543 | 0.016 | 19643 | | | | | | | | |

$^{(1)}$Threshold for statistical significance;
ns: >0.05, Not significant;
*: 0.01 to 0.05, Significant;
**: 0.001 to 0.01, Very significant;
***: <0.001, Extremely significant

TABLE 5

Effect of compound EPA EE on staurosporine-induced caspase-3/7 activity in NHDF

| Treatment | | Basic data | | | | | | | | Normalized data | | | |
|---|---|---|---|---|---|---|---|---|---|---|---|---|---|
| | | Caspase-3/7 activity (Fluorescence) | Caspase-3/7 activity − Background (Fluorescence) | Proteins | | Caspese-3/7 activity/proteins | Mean | sem | % stimulated control | sem (%) | P$^{(1)}$ | % inhibition | sem (%) | P$^{(1)}$ |
| Test compound | Concentration | 380 nm/440 nm− AU | 380 nm/440 nm− AU | (mg/ml) | (mg) | (AU/mg) | (AU/mg) | (AU/mg) | | | | | |
| Background Assay buffer + caspase-3/7 substrate | * | 322<br>320<br>309 | * | * | * | * | * | * | * | * | * | * | * | * |
| Positive control Recombirant human active Caspese-3 | 50 ng/ml | 10975<br>11067<br>11122 | 10658<br>10750<br>10805 | * | * | * | * | * | * | * | * | * | * | * |
| Non-stimulated condition Control | * | 473<br>494<br>468 | 156<br>177<br>151 | 0.663<br>0.697<br>0.743 | 0.020<br>0.021<br>0.022 | 7845<br>8446<br>6795 | 7695 | 483 | 3 | 1 | *** | 100 | 1 | *** |
| Control | * | 1414<br>1523<br>1366 | 1097<br>1206<br>1049 | 0.412<br>0.421<br>0.434 | 0.012<br>0.013<br>0.013 | 88754<br>95521<br>80551 | 88275 | 4328 | 100 | 5 | * | 0 | 5 | * |
| EPA EE | 0.001 µg/ml | 1457<br>1667<br>1637 | 1140<br>1350<br>1320 | 0.379<br>0.351<br>0.396 | 0.011<br>0.011<br>0.012 | 100237<br>128199<br>111084 | 113173 | 8139 | 128 | 9 | ns | −31 | 10 | ns |
| | 0.01 µg/ml | 1359<br>1476<br>1472 | 1042<br>1159<br>1155 | 0.388<br>0.434<br>0.429 | 0.012<br>0.013<br>0.013 | 89522<br>89043<br>89708 | 89425 | 198 | 101 | 0 | ns | −1 | 0 | ns |
| | 0.1 µg/ml | 1474<br>1382<br>1558 | 1157<br>1065<br>1241 | 0.463<br>0.445<br>0.462 | 0.014<br>0.013<br>0.014 | 83312<br>79809<br>89506 | 84209 | 2035 | 95 | 3 | ns | 5 | 4 | ns |
| | 1 µg/ml | 1423<br>1604<br>1486 | 1106<br>1287<br>1169 | 0.422<br>0.443<br>0.446 | 0.013<br>0.013<br>0.013 | 87358<br>96851<br>87370 | 90527 | 3162 | 103 | 4 | ns | −3 | 4 | ns |
| | 10 µg/ml | 1335<br>1264<br>1458 | 1018<br>947<br>1141 | 0.435<br>0.411<br>0.361 | 0.013<br>0.012<br>0.011 | 78044<br>76787<br>105337 | 86723 | 9314 | 98 | 11 | ns | 2 | 12 | ns |
| | 100 µg/ml | 807<br>843<br>1068 | 490<br>526<br>751 | 0.552<br>0.456<br>0.493 | 0.017<br>0.014<br>0.015 | 29572<br>37623<br>50763 | 39319 | 6176 | 45 | 7 | ** | 61 | 8 | ** |

$^{(1)}$Threshold for statistical significance;
ns: >0.05, Not significant;
*: 0.01 to 0.05, Significant;
**: 0.001 to 0.01, Very significant;
***: <0.001, Extremely significant As shown in FIG. 1, at the concentration of 100 μg/ml, compounds 15(S)-HEPE EE and EPA EE both displayed a clear inhibitory effect on caspase-3/7 activity (with a stronger effect for compound 15(S)-HEPE EE).

What is claimed is:

1. A method of treating cancer in a subject in need thereof, the method comprising administering to the subject 15-HEPE and/or derivative thereof or a composition comprising 15-HEPE and/or derivative thereof, wherein the derivative thereof is an esterified form of 15-HEPE, a triglyceride form of 15-HEPE, or combination thereof.

2. The method of claim 1, wherein the 15-HEPE is in free acid form.

3. The method of claim 1, wherein the esterified form is an alkyl ester form.

4. The method of claim 3, wherein the esterified form is ethyl ester.

5. The method of claim 1, wherein the cancer is selected from the group consisting of liver cancer, hepatocellular carcinoma, skin cancer, prostate cancer, breast cancer, carcinoma, sarcoma, leukaemia, lymphoma-myeloma and CNS cancer.

6. The method of claim 1, wherein the 15-HEPE and/or derivative thereof comprises 15(S)-HEPE.

7. The method of claim 1, wherein the 15-HEPE and/or derivative thereof comprises 15(R)-HEPE.

8. A method of sensitizing cancer cells to radiation therapy in a subject in need thereof, the method comprising administering to the subject 15-HEPE and/or derivative thereof or a composition comprising 15-HEPE and/or derivative thereof and concurrently or thereafter treating cancer cells in the subject with radiation, wherein the derivative thereof is an esterified form of 15-HEPE, a triglyceride form of 15-HEPE, or combination thereof.

* * * * *